United States Patent [19]
Chase

[11] Patent Number: 5,630,436
[45] Date of Patent: May 20, 1997

[54] APPARATUS FOR CLEANING LONG TUBULAR MEDICAL INSTRUMENTS

[76] Inventor: John G. Chase, 1620 E. Dorchester, Palm Harbor, Fla. 34684

[21] Appl. No.: 574,217

[22] Filed: Dec. 18, 1995

[51] Int. Cl.⁶ ..................................................... B08B 3/12
[52] U.S. Cl. ...................... 134/111; 134/169 R; 134/170
[58] Field of Search .................. 134/111, 169 R, 134/169 A, 169 C, 170; 422/33, 292, 300

[56]  References Cited

U.S. PATENT DOCUMENTS

| | | | |
|---|---|---|---|
| 4,064,886 | 12/1977 | Heckele | 134/169 C X |
| 4,589,403 | 5/1986 | Ouchi et al. | |
| 5,310,524 | 5/1994 | Campbell et al. | 134/170 X |
| 5,339,845 | 8/1994 | Huddas | 134/169 A |
| 5,492,672 | 2/1996 | Childers et al. | 422/33 X |
| 5,494,530 | 2/1996 | Graf | 134/170 X |
| 5,505,218 | 4/1996 | Steinhauser et al. | 134/170 X |
| 5,511,568 | 4/1996 | Bowman et al. | 134/169 C X |
| 5,533,539 | 7/1996 | Sutter et al. | 134/170 X |
| 5,554,228 | 9/1996 | Giordano et al. | 134/170 X |

*Primary Examiner*—Philip R. Coe
*Attorney, Agent, or Firm*—Harold D. Shall

[57] ABSTRACT

Apparatus for cleaning long tubular instruments including an ultrasonically agitated sump containing cleaning solution into which the instrument to be cleaned is placed. A pump and filter arrangement is connected to an end of the instrument to impose a pulsating partial vacuum thereon and draw cleaning fluid through the full length of the instrument. The filtered cleaning solution is then returned to the sump.

5 Claims, 3 Drawing Sheets

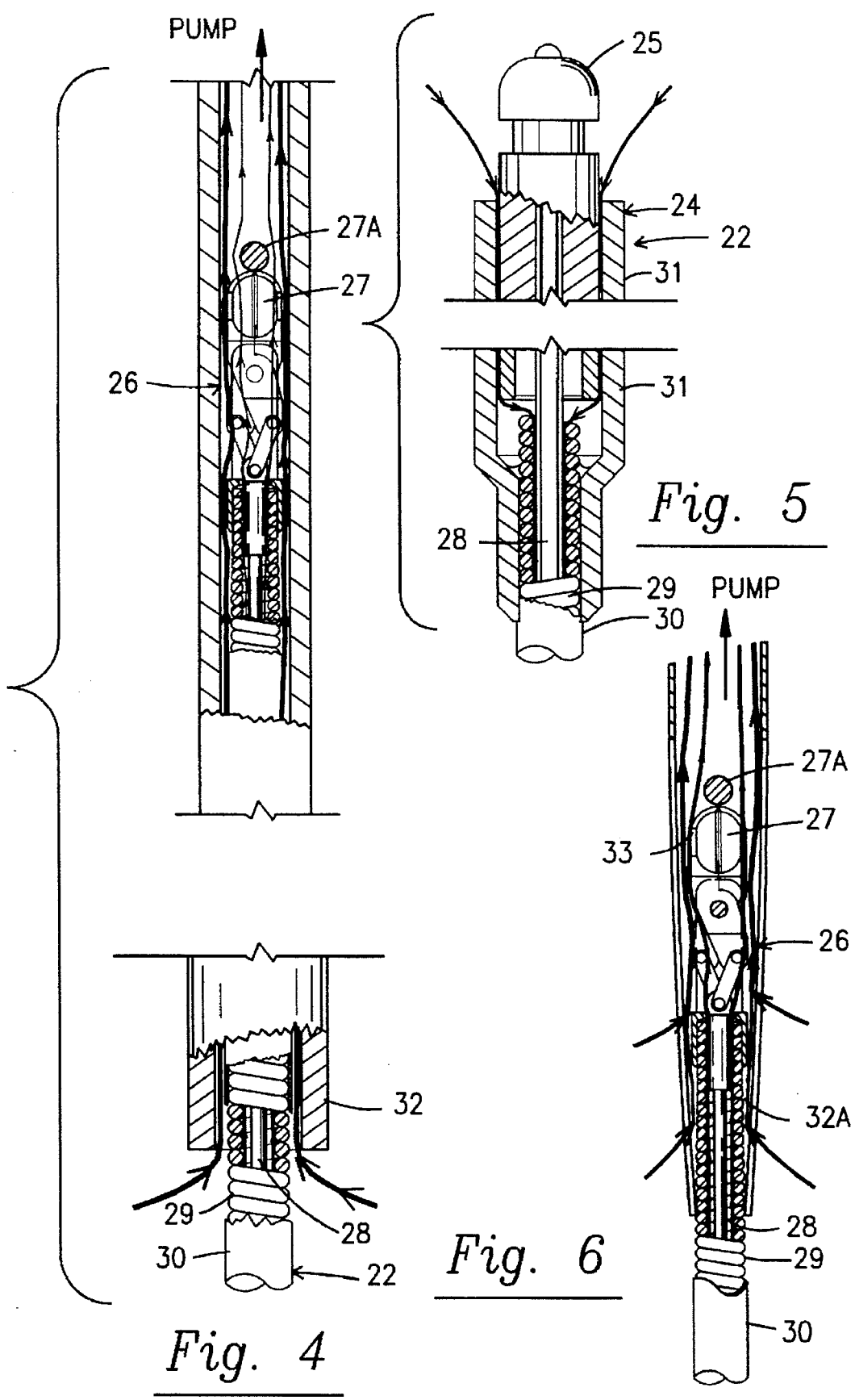

APPARATUS FOR CLEANING LONG TUBULAR MEDICAL INSTRUMENTS

BACKGROUND OF THE INVENTION

1.) Field of the Invention

This invention relates to cleaning of tubular medical instruments such as endoscopic biopsy forceps instruments and laparascopic surgical instruments.

2.) Description of the Prior Art

Instruments of the above type, for example a typical endoscopic surgical instrument, has an outer flexible tubular body made from a length of coiled, closely fitting helical spring whose inside diameter is approximately 1.0 mm and whose length is approximately 200 cm. A 0.5 mm diameter wire is slidingly mounted inside of the tubular body and is connected to a pair of snippers at the distal end of the wire and an operating handle is connected to the proximal end of the wire. This is conventional construction and the intimate details of the instrument beyond the foregoing does not form a part of this invention. When these instruments are conventionally used within the body, fluids not only are deposited on the outside of the tubular instrument but also tend, because of the body pressure on these fluids and also through capillary action, to enter the space between the control wire and the inner surface of the hollow tubular body made of the coiled spring. This material within the tubular body has not been properly and completely removed by prior art cleaning methods. Normal cleaning practices to remove body fluids include soaking, scrubbing and ultrasonic cleaning in such agents as detergents and enzyme cleaners. However, the materials which have entered the tubular member are not adequately cleaned by these methods. Medical facilities tend to deal with this situation by frequent replacement of instruments or by using disposable instruments, which is a costly and wasteful means for dealing with the situation.

SUMMARY OF THE INVENTION

It is an object of this invention to provide apparatus for cleaning long medical instruments having a tubular outer member and an operative member within the outer member.

It is another object of this invention to provide such an apparatus for providing a flow of cleaning fluid within the tubular member for the full length thereof.

It is a further object of this invention to provide such an apparatus that subjects the tubular member and the cleaning fluid to ultrasonic vibrations during such cleaning operation.

It is yet another object of this invention to provide such an apparatus wherein the tubular members to be cleaned are placed in an ultrasonically vibrated sump containing cleaning fluid while applying a vacuum thereto so that the cleaning fluid is drawn into the tubular member and then filtered before being returned to the sump.

Further and other objects of this invention will become apparent from a review of the following drawings, specification and claims.

BRIEF DESCRIPTION OF THE DRAWINGS

FIG. 4 is an enlarged sectional view of the distal end of the instrument shown in FIG. 3 with a suction tube secured thereto;

FIG. 5 is a cross sectional view of the proximal end of the instrument of FIG. 4; and FIG. 6 is a cross sectional view of the distal end of a different long tubular instrument with a different suction tube connected thereto.

DETAILED DESCRIPTION OF THE PREFERRED EMBODIMENT

The following description is of a cleaning machine according to this invention showing how it cleans a typical biopsy forceps.

Figure 1:
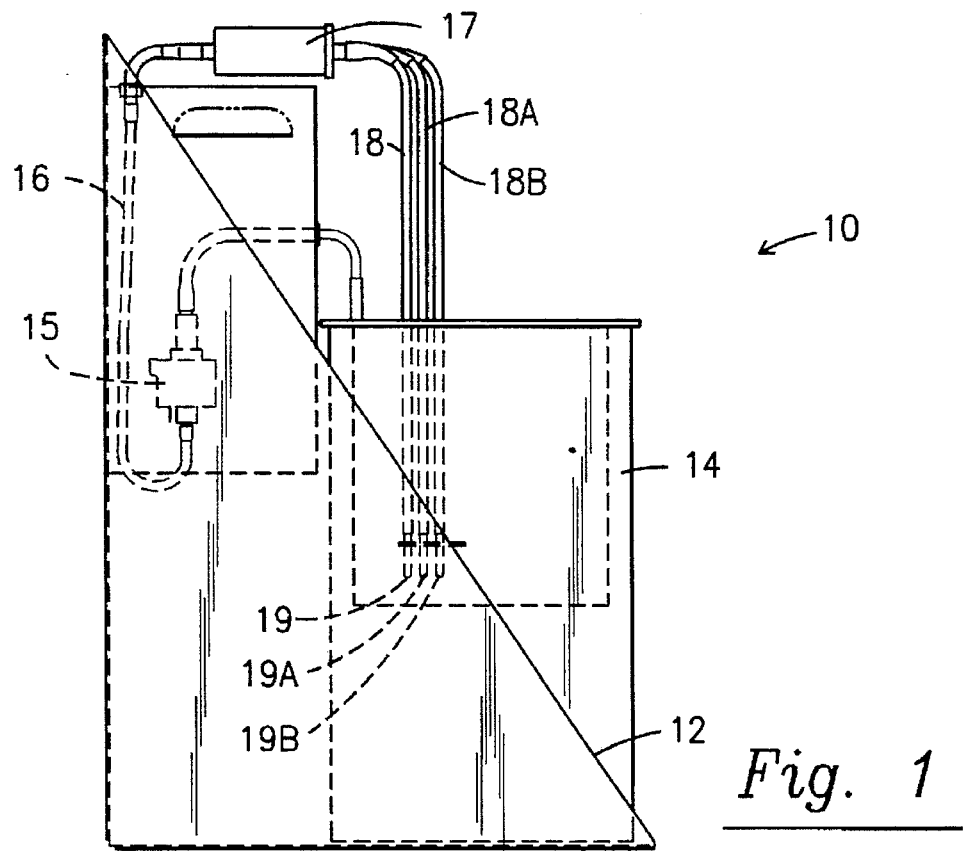
FIG. 1 is a side elevational view of a machine incorporating the features of this invention.
Figure 2:
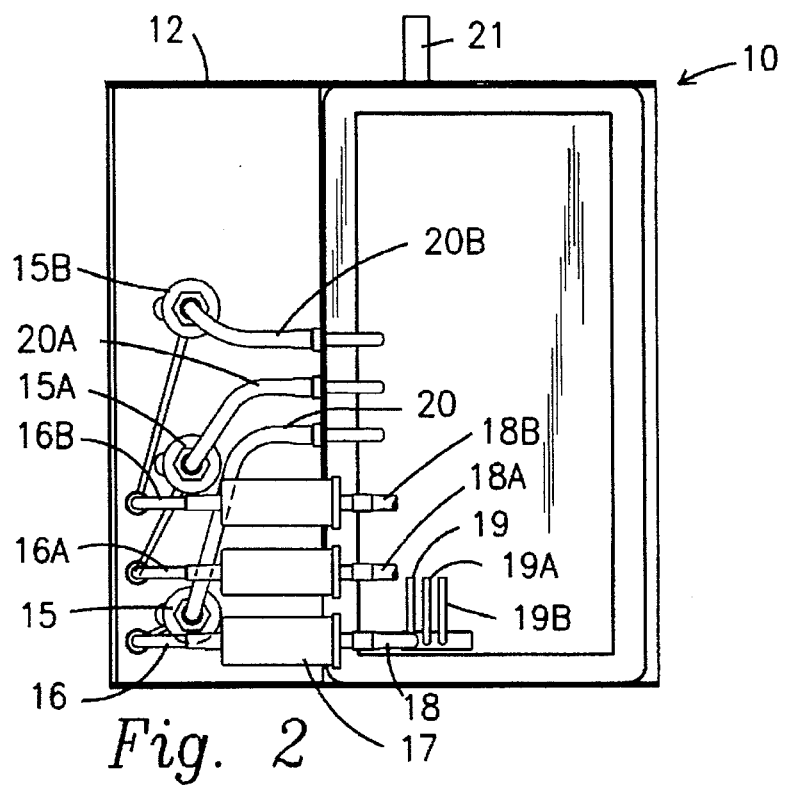
FIG. 2 is a plan view of the machine of FIG. 1.

Referring now to the drawings, and more particularly to FIGS. 1 and 2, a ultrasonic vacuum-flow-inducing cleaning machine is shown generally at 10 and includes a supporting frame 12, and an ultrasonic generating cleaning fluid containing sump 14 of suitable size to receive a number of tubular instruments to be completely submerged in the cleaning fluid, which sump 14 is securely carried by the frame 12. A suitable sump may be obtained from the Sonicor Instrument Corp. of Copiaque, N.Y. under the designation of a SC150 Ultrasonic Cleaner.

A plurality of positive displacement pumps, shown at 15, 15A and 15B, one for each instrument to be cleaned, are suitably secured to the frame 12 and each is connected by a pipe 16, 16A and 16B, respectively, to a separate filter 17, 17A and 17B, and from each of the filters a suction line 18, 18A and 18B, respectively, extends into the sump 14, where each of the suction lines is connected to a connecting fitting 19, 19A and 19B respectively. The output from the pumps 15, 15A and 15B are connected to return lines 20, 20A and 20B, respectively, which conducts the output from the pumps back into the sump 14. A drain line 21 extends from the bottom side of the sump 14 to drain the cleaning solution therefrom when desired.

Pumps 15, 15A and 15B suitable for this invention may be obtained from the Milton Roy Company of Ivyland, Pa. under the designation of Compact NMSolenoid Pump, while filters suitable for this invention may be obtained from Filtertek, Inc. of Hebron, Ill. under the designation of Large In-Line Filter #56900.

Referring now to FIGS. 3–6, the sump 14 is shown receiving a long tubular medical instrument such as an endoscopic biopsy forceps 22. The forceps 22 has a proximal end 24 which terminates in a manually manipulated knob 25 and a distal end 26 terminating in a forceps 27 which is manipulated by the knob 25 through the connection with the forceps 27 by a wire 28 mounted for reciprocal and rotative movement in a coiled helical spring member 29 surrounded by a conventional impervious outer coating 30. At the proximal end, a conventional outer sleeve 31 is secured at its distal end to the coil spring 29 and outer coating 30, which sleeve 31 sliding receives the knob 25.

Figure 3:
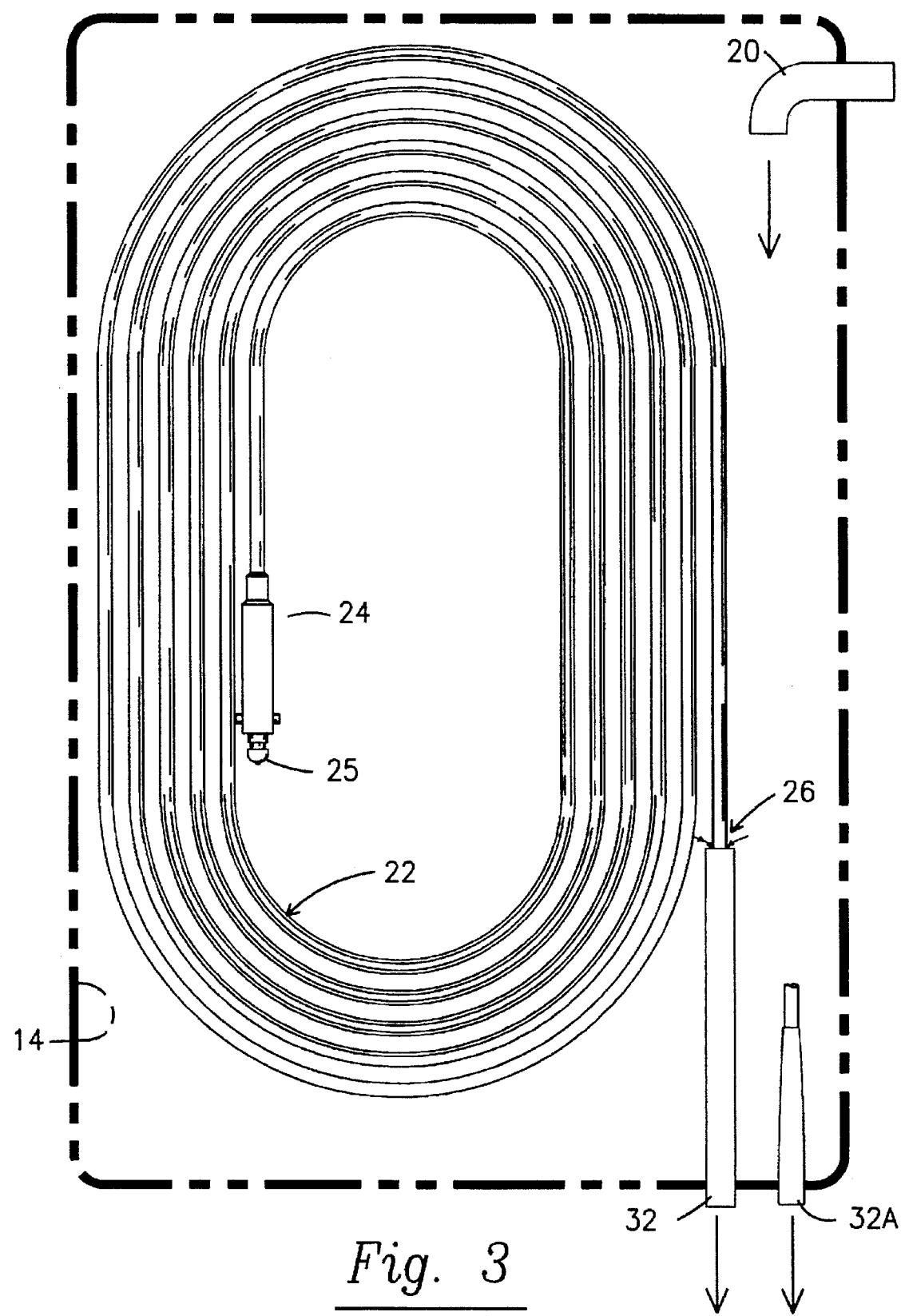
FIG. 3 is a diagrammatic plan view of the sump of the machine of FIG. 1 with a long tubular medical instrument shown therein.

As seen in FIG. 3, the forceps 22 is placed in the sump 14 and immersed in a cleaner such as Klenzyme available from Calgon Vestal Laboratories of St. Louis, Mo.

A suction tube, shown at 32 and 32A in FIG. 3 and more fully described hereinafter, is slipped over the distal end 26 of the forceps 22. The suction tube 32 or 32A is confluently connected to one of the connecting fittings 19, 19A or 19B and from the latter through a filter 17, 17A or 17B to a pump 15, 15A or 15B and from the latter through a return line 20, 20A or 20B to the sump 14. As seen in FIG. 4, the suction tube 32 closely fits, yet is slightly spaced from the periphery of the distal end of the tubular instrument 22 and when suction is applied by the pump 15, cleaning fluid flows through two paths; a first path between the periphery of the instrument 22 and the suction tube 32 to thereby clean the periphery of the distal end of the instrument and, with reference to FIG. 5, cleaning solution enters between the knob 25 and the outer sleeve 31 to thereby flow into the instrument 22 between wire 28 and the coiled helical spring 29 and from there out through the suction tube 32 to thereby clean the entire inside of the instrument.

The suction tube 32 must be designed to fit the periphery of the particular instrument 22 being cleaned. Referring to FIG. 6, a more widely applicable suction tube 32A is shown which need not be so closely fit to each instrument. More particularly, the suction tube 32A has a plurality of longitudinal slots 33 therein extending inwardly from the outer end thereof whereby upon the application of vacuum to the tube 32A the slots will allow the end of the tube to collapse on the outside of the instrument, while the slots 33 will allow cleaning solution to flow thereinto. Both the suction tubes 32 and 32A have a physical stop 27A secured therein to limit inward movement of the instrument 22.

The ultrasonically agitated cleaning solution, enhanced in its agitating forces by the 30 Hz pulsating partial vacuum induced inside the instrument by the associated solenoid pump, loosens whatever debris is on and in the instrument so that the flow of cleaning solution can flush the debris away and into the filters 17, 17A or 17B where such debris is removed from the system and the filtered solution is returned to the sump.

Although the above description relates to a presently preferred embodiment, numerous changes can be made therein without departing from the scope of this invention as claimed in the following claims.

What is claimed is:

1. Apparatus for cleaning long tubular instruments comprising, a) an ultrasonically agitated sump, b) a cleaning fluid in said sump, c) confluently connected pump and filter means, d) suction means extending from said filter means into said fluid in said sump for confluent connection to one of the ends of the instrument to be cleaned, e) and return means confluently connecting said pump means to said sump.

2. An apparatus according to claim 1 wherein said pump means is of the rapidly intermittent type whereby said pump means creates a pulsating partial vacuum in said suction means extending from said filter means into said fluid.

3. An apparatus according to claim 2 wherein said pump means is a solenoid pump.

4. An apparatus according to claim 1 wherein said suction means has a distal end remote from said filter and extending into said fluid, said distal end including slit means whereby said distal end may flex to fit the periphery of the instrument to be cleaned.

5. Apparatus for cleaning long tubular instruments comprising, a) a sump, b) a cleaning fluid in said sump, c) confluently connected pump and filter means, d) suction means extending from said filter means into said fluid in said sump for confluent connection to one of the ends of the instrument to be cleaned, e) and return means confluently connecting said pump means to said sump, and f) wherein said pump means is of the rapidly intermittent type whereby said pump means creates a pulsating partial vacuum in said suction means extending from said filter means into said fluid.

* * * * *